US00PP20061P3

(12) United States Plant Patent
Hambali

(10) Patent No.: US PP20,061 P3
(45) Date of Patent: Jun. 9, 2009

(54) ***CALATHEA* PLANT NAMED 'TWYCA0026'**

(50) Latin Name: ***Calathea loesenerii*×*Calathea roseopicta***
Varietal Denomination: TWYCA0026

(75) Inventor: Gregori G. Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 75 days.

(21) Appl. No.: 11/894,571

(22) Filed: Aug. 21, 2007

(65) Prior Publication Data

US 2009/0055983 P1 Feb. 26, 2009

(51) Int. Cl.
*A01H 5/00* (2006.01)

(52) U.S. Cl. ..... Plt./375

(58) Field of Classification Search ..... Plt./375
See application file for complete search history.

(56) References Cited

U.S. PATENT DOCUMENTS

PP8,836 P * 7/1994 Lamb ..... Plt./375

* cited by examiner

*Primary Examiner*—Wendy C Haas
(74) *Attorney, Agent, or Firm*—Jondle & Associates, P.C.

(57) ABSTRACT

A new *Calathea* plant particularly distinguished by pink and green bracted inflorescences which are held high above the foliage, sturdy and upright growth habit, large ovate to elliptical leaves with dark green margins and broad grey-green elliptical centers, is disclosed.

1 Drawing Sheet

Genus and species: *Calathea loesenerii*×*Calathea roseopicta.*
Variety denomination: 'TWYCA0026'.

BACKGROUND OF THE NEW PLANT

The present invention comprises a new and distinct cultivar of *calathea*, botanically known as *Calathea loesenerii*× *Calathea roseopicta,* and hereinafter referred to by the cultivar name 'TWYCA0026'. The new cultivar originated from a hybridization made in October 1998 in Bogor, Indonesia. The female parent was *Calathea loesenerii.* The male parent was 'Rosy', *Calathea roseopicta* (U.S. Plant Pat. No. 8,836).

A single plant selection was chosen for further evaluation and for asexual propagation in August 2000.

The new cultivar was first propagated in December 2001 in Sebring, Fla. and has been asexually reproduced repeatedly by division and tissue culture in Sebring, Fla. over two to three generations. The present invention has been found to retain its distinctive characteristics through successive asexual propagations.

SUMMARY OF THE INVENTION

The following are the most outstanding and distinguishing characteristics of this new cultivar when grown under normal horticultural practices in Sebring, Fla.

1. Pink and green bracted inflorescences which are high above the foliage;
2. Sturdy and upright growth habit; and
3. Large ovate to elliptical leaves with dark green margins and broad grey green elliptical center

DESCRIPTION OF PHOTOGRAPH

This new *Calathea* plant is illustrated by the accompanying photograph which shows the overall plant habit including blooms, buds, and foliage of the plant; the colors shown are as true as can be reasonably obtained by conventional photographic procedures.

DESCRIPTION OF THE NEW CULTIVAR

The following detailed description sets forth the distinctive characteristics of 'TWYCA0026'. The data which define these characteristics were collected from asexual reproductions carried out in Apopka, Fla. The data were obtained in April 2006 from 12 months old plants grown in 6-inch pots from a 13 week old tissue culture derived older line. The plants were grown in a greenhouse with fiberglass panel siding with inflated double poly roof with a modine heating, fan and pad cooling system. Color references are to The Royal Horticultural Society Colour Chart, 2001 edition.

DETAILED BOTANICAL DESCRIPTION OF THE NEW PLANT

Classification:
*Family.*—Marantaceae.
*Botanical name.—Calathea loesenerii*×*Calathea roseopicta.*
*Common name.—Calathea .*
Parentage:
*Female parent.—Calathea loesenerii.*
*Male parent of the initial cross.—Calathea roseopicta.*
Growth:
*General.*—Tropical flowering potted plant; plant is suitable for use in shaded tropical and frost-free landscapes.

*Time to flower.*—12 months to finish flowering, starting from a 13-week old liner from tissue culture.

*Appropriate container.*—15 cm to 20 cm pots; suitable for use in shaded tropical landscapes.

Plant Description:

*Life cycle.*—Herbaceous perennial.

*Habit.*—Upright, wider than tall, inverted triangle, densely leafy; inflorensces upright and held above and among the foliage in the center of the plant; upright whorls of leaves arise from underground rhizome.

*Height.*—44.0 cm to 50.0 cm.

*Spread (including flowers).*—60.0 cm to 65.0 cm.

*Root color.*—RHS 199A (Dark brown); tips RHS 154C to RHS 154D.

Branches:

*Number.*—8 basal branches.

*Length.*—Variable depending upon age.

*Lateral branch diameter.*—1.2 cm.

Stems (Rhizomes):

*Description.*—Cylindrical, round in traverse section.

*Aspect.*—Horizontal, underground rhizome becoming upturned, vertical at tip.

*Strength.*—Thick, tough and fibrous.

*Internode length.*—1.0 cm to 3.2 cm.

*Color.*—RHS N170D tinged with RHS 182D.

Leaves:

*Arrangement.*—Alternate, closely spaced in vertical ranks, rosette, with one to 3 per lateral branch depending on age of the branch.

*Shape.*—Simple, elliptical.

*Apex.*—Cuspidate.

*Base.*—Obtuse.

*Margin.*—Entire, wavy.

*Size.*—Length: 18.0 cm to 24.0 cm. Width: 14.0 cm to 16.3 cm.

*Color.*—Immature leaf: Upper surface: Leaf margin of RHS 146A to RHS 147A with RHS 192A in the center; may be faintly tinged with RHS 58A. Lower surface: RHS N186C. Mature leaf: Upper surface: Leaf margin darker than but closest to RHS 147A with RHS 191B to RHS 191C in the center. Lower surface: RHS N186C.

*Venation.*—Type: Pinnate. Color: Upper surface: Midrib: RHS 147C. Primary veins: RHS 147B to RHS 147C. Lower surface: Midrib: RHS N199A tinged with RHS N186C. Primary veins: RHS N186C.

*Texture.*—Upper surface: Glossy to shiny, concave between primary veins resulting in a slightly textured look. Lower surface: Matte, dull.

*Surface pubescence.*—Absent.

*Petiole.*—Length: 23.0 cm to 30.0 cm. Diameter: 0.5 cm. Texture: Smooth. Color: RHS 200B flushed with RHS N186C.

*Petiole sheath.*—Encircles the rhizome and extends up the petiole to within 10.0 cm to 15.0 cm of the base of the leaf. Color: Outside: RHS 200B to RHS N186C. Inside: Smooth, shiny RHS 147B flushed with RHS 187B.

*Cataphylls.*—Shape: Lanceolate. Apex: Acute. Base: Sessile, clasping rhizome. Length: 8.0 cm to 12.0 cm. Diameter: 2.2 cm. Color: Outside: RHS 186C. Inside: Smooth, shiny RHS 147C flushed with RHS 187B.

*Geniculum.*—General: The orientation of the leaf to the petiole is variable, as the geniculum bends. During the night and early morning the geniculum is straight, and the leaf is held nearly vertical above the foliage. During the day, the geniculum is bent, and the leaf curves outward. Length: 3.2 cm. Diameter: 0.48 cm. Color: RHS 200B flushed with RHS N186C.

Flower Bud:

*Size.*—Length: 1.2 cm. Diameter: 0.35 cm.

*Shape.*—Elongated, elliptical.

*Color.*—RHS 1D (Yellow) in-the center, RHS155B at the base; and the tip is translucent white.

*Quantity of flowers and buds per plant.*—9 spikes are present; 504 flowers and buds per plant.

Inflorescence:

*Time to produce a finished flowering plant.*—Lastingness of the flowers on the plant: Individual flowers last about one day before shrivelling.

*Flowering season.*—Spring and fall 1 to 3 flowers may open simultaneously per inflorescence per day over a period of about 8 weeks.

*Arrangement.*—Inflorescence emerges from the center of the whorl of leaves. Flowers emerge from short branch spikes under colourful bracts atop a tall upright spike.

*Inflorescence type.*—Tall, upright, terminally bracted spike; bracts arranged in closely spaced vertical ranks occupying the upper 6.5 cm of the spike.

*Inflorescence height.*—52.0 cm.

*Inflorescence width.*—7.5 cm from tip to tip of bracts across top of inflorescence.

*Number of flowers per inflorescence.*—56.

*Fragrance.*—Absent.

*Form.*—Tube-like.

*General.*—Self-cleaning.

*Flowering habit.*—Tips of petals and staminods emerge from branch spikes under fertile bracts; flowers last about one day before fading and shriveling.

*Aspect.*—Outward.

*Shape.*—Tube like; staminodes and petals curve outward.

*Diameter.*—1.5 cm across the face of the flower; tube of flower is 0.2 cm.

*Height.*—3.0 cm.

Flowers:

*Petals.*—General: 3 petals per flower; tube-like with a translucent, delicate appearance that curves outward at the tips. Size: Length: 2.5 cm. Width: 0.3 cm. Shape: Narrow elliptic. Apex: Acute. Margin: Entire. Texture: Smooth. Color: General: Translucent white, fading from RHS 199C to RHS 199D and becoming RHS 200A.

*Sepals.*—General: Composed of 3 sepals; translucent, pale white, crystalline with a tube-like arrangement. Shape: Narrow elliptic to linear. Apex: Acute. Base: Sessile. Margin: Entire. Length: 1.5 cm. Width: 0.2 cm. Texture: Both sides are smooth. Color: Translucent white.

*Peduncle.*—Length: 50.0 cm. Diameter: 0.4 cm. Angle: Straight upright. Strength: Tough flexible. Texture: Coarse, dull to matte. Color: RHS 186A.

*Bracts.*—General: Terminal bracts uppermost on raceme, subtended by fertile bracts with underlying branch spikes. Terminal bracts: Quantity: 7. Length: 4.4 cm. Width: 2.0 cm. Shape: Ovate. Apex: Acute. Base: Sessile. Margin: Entire, smooth. Color: Upper surface: Margin RHS 186B (Pink); Center RHS 186B tinged with RHS 137A to RHS 190A. Lower surface: RHS 186B to RHS186C with RHS 186C margin. Texture: Upper surface: Smooth. Lower surface: Slightly rough. Fertile bracts: Quantity: 14. Length: 2.7 cm. Width: 2.8 cm. Shape: Broadly obovate. Apex: Emarginate. Base: Sessile. Margin: Entire, smooth. Color: Upper surface: RHS 186C with the center tinged with RHS 138B. Lower surface: RHS186B to RHS 186C, with the center tinged with RHS137C. Texture: Upper surface: Smooth. Lower surface: Slightly rough.

Reproductive organs:

*Staminode.*—3 thin, crystalline, delicate, with a tube-like arrangement that is flared outward and reflexed at the tips. Shape: Two are spatulate with emarginated tips, one is short reduced, linear, cupped. Margin: Entire. Length: 2.9 cm; reduced staminode is 2.5 cm. Width: 0.65 cm; reduced staminode is 0.3 cm Texture: Smooth Color: Spatulate staminodes are white flushed with RHS 76B to RHS 76C; reduced staminodes are white tinged with RHS 76B to RHS 76C.

*Stamens.*—Quantity: 1. Anther shape: Lanceolate. Anther length: 0.25 cm. Anther width: 0.08 cm. Anther color: RHS 162B. Pollen amount: Sparse. Pollen color: White.

*Pistils.*—Quantity: 1. Length: 2.8 cm. Stigma shape: Elliptic, cupped. Stigma color: White. Style length: 2.7 cm. Style diameter: 0.1 cm. Style color: White. Ovary: Inferior. Color: White. Length: 0.18 cm. Width: 0.2 cm.

Fruit and Seed Set: Has not been observed.

Disease and Insect Resistance: Resistance and susceptibility is typical of the species.

COMPARISON WITH PARENTAL AND COMMERCIAL CULTIVARS

'TWYCA0026' differs from the male parent *Calathea roseopicta* 'Rosy' in that 'TWYCA0026' has inflorescences that are attractive and above the foliage while 'Rosy' has inconspicuous inflorescences that are well below the foliage. 'TWYCA0026' is taller and has an upright growth habit while 'Rosy' is shorter with a spreading growth habit. 'TWYCA0026' has larger leaves that are more elliptical in shape, while 'Rosy' has smaller leaves that are more round in shape. Additionally, 'TWYCA0026' has juvenile leaves that are tinged with a pinkish color, while 'Rosy' has juvenile leaves that are intensely flushed with pink.

'TWYCA0026' differs from the female parent *Calathea loesenerii* in that 'TWYCA0026' has leaves that are broadly elliptic with silver markings while *C. loesenarii* has leaves that are plain green. Additionally, 'TWYCA0026' has inflorescences with greenish pink bracts while *C. loesenarii* has inflorescences with in pink bracts.

I claim:

1. A new and distinct cultivar of *Calathea* plant as shown and described herein.

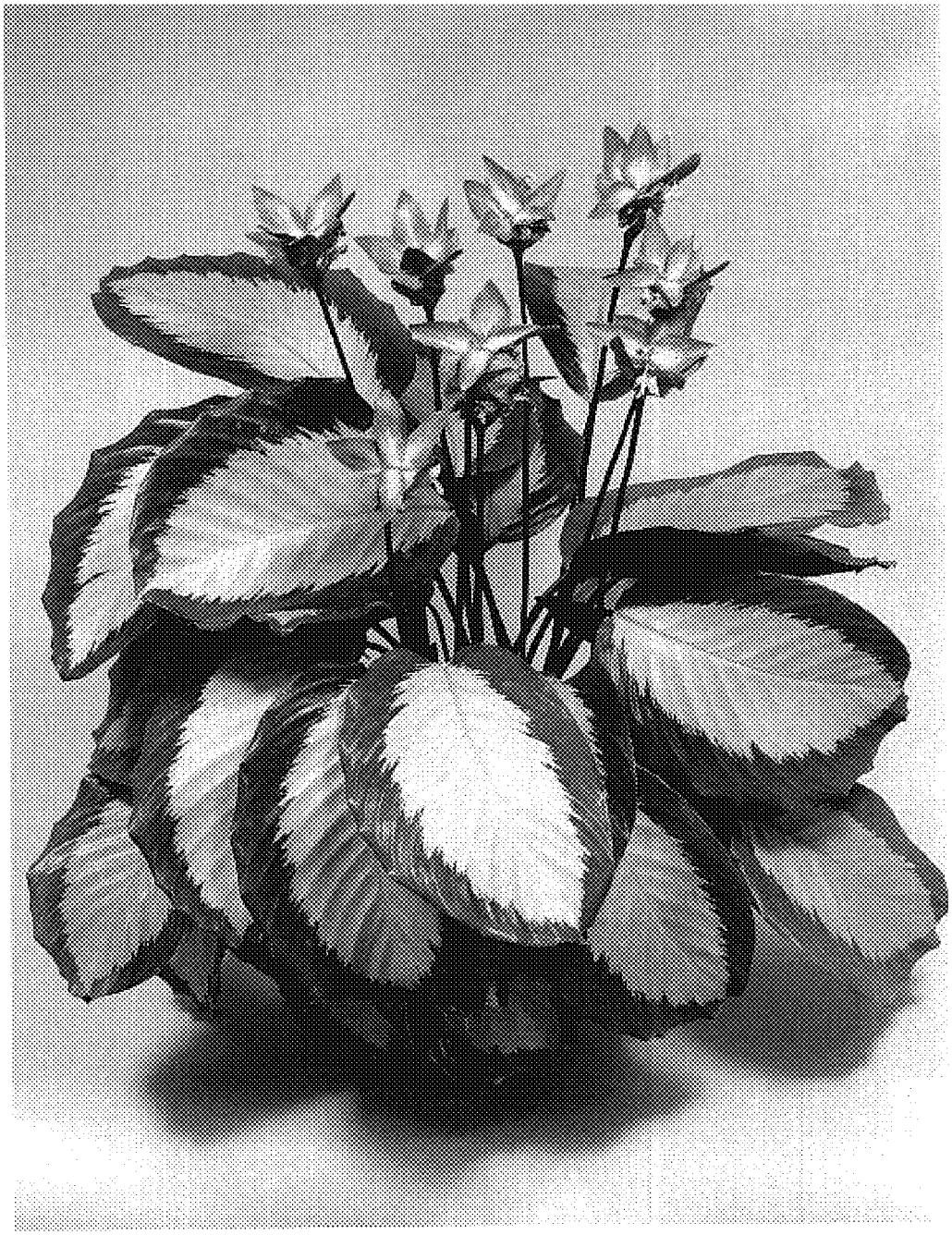

* * * * *